Figure 1:
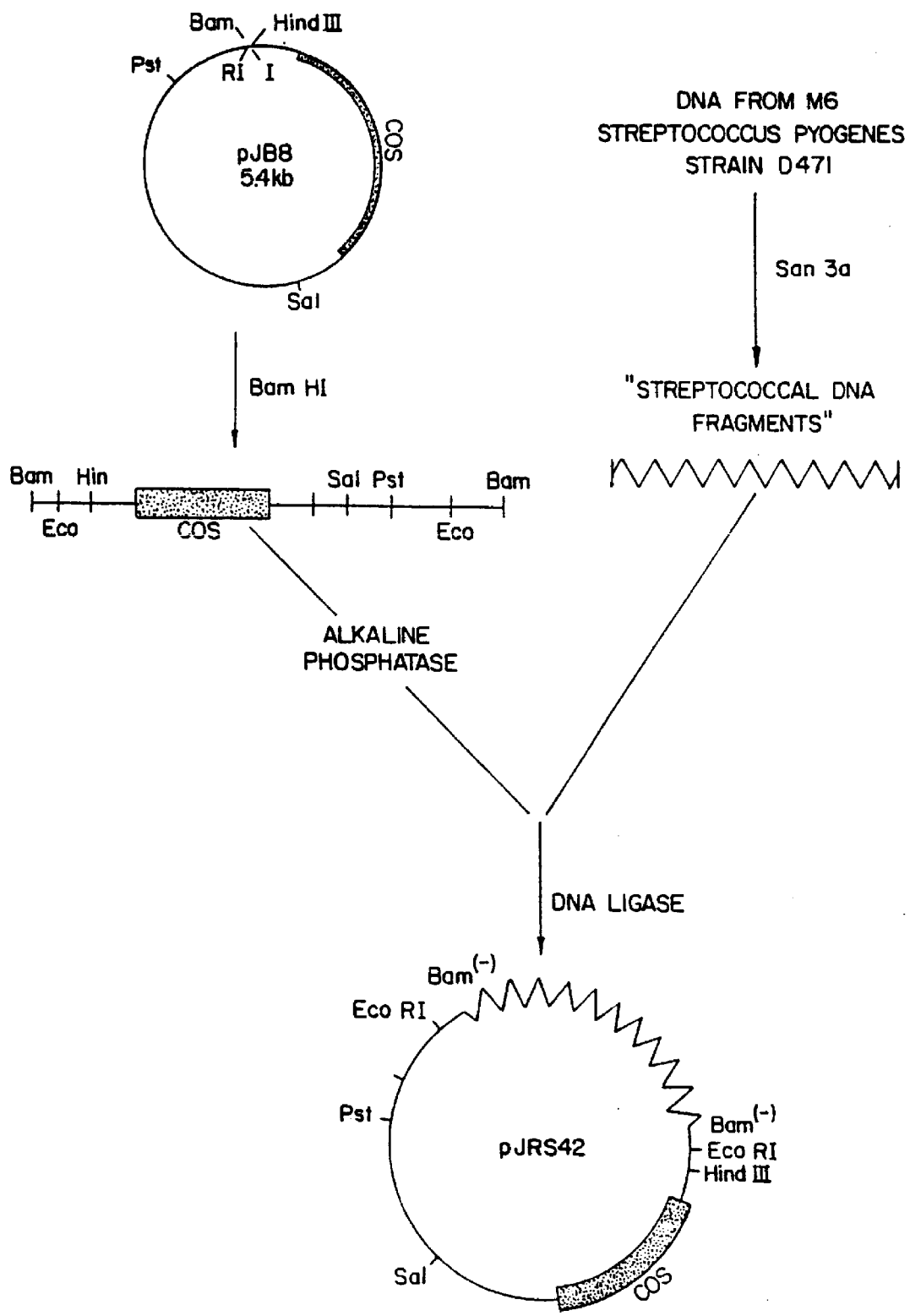

United States Patent [19]
Scott et al.

[11] Patent Number: 5,840,314
[45] Date of Patent: Nov. 24, 1998

[54] PRODUCTION OF STREPTOCOCCAL M PROTEIN

[75] Inventors: June Rothman Scott, Atlanta, Ga.; Vincent Angelo Fischetti, West Hempstead, N.Y.

[73] Assignees: The Rockefeller University, New York, N.Y.; Emery University, Atlanta, Ga.

[21] Appl. No.: 200,914

[22] Filed: Feb. 22, 1994

Related U.S. Application Data

[63] Continuation of Ser. No. 61,812, May 13, 1993, abandoned, which is a continuation of Ser. No. 800,890, Nov. 27, 1991, abandoned, which is a continuation of Ser. No. 604,353, Oct. 26, 1990, abandoned, which is a continuation of Ser. No. 456,189, Dec. 15, 1989, abandoned, which is a continuation of Ser. No. 141,586, Jan. 7, 1988, abandoned, which is a division of Ser. No. 621,716, Jun. 18, 1984, Pat. No. 4,784,948, which is a continuation-in-part of Ser. No. 521,962, Aug. 10, 1983, abandoned.

[51] Int. Cl.$^6$ .......................... A61K 39/09; C12P 21/06; C07K 1/00
[52] U.S. Cl. ................. 424/244.1; 435/69.3; 435/252.3; 530/350
[58] Field of Search ........................ 424/244.1; 435/69.3, 435/252.3; 530/350, 806, 825

[56] References Cited

U.S. PATENT DOCUMENTS 4,284,537  8/1981  Beachey ...................................... 260/6

OTHER PUBLICATIONS

Manjula et al, "Studies on Group A Streptococcal M–proteins: purification of type 5M–protein and comparison of its amino terminal sequence with two immunologically virulent M–proteins molecules," Journal of Immunol. vol. 124, pp. 261–267, 1980.
Berzofsky et al; Science 229:932–940, 1985.
Stern P.S. TIBTECH 9:163–168, 1991.
Beachey et al, J Immunol 136(6):2287–2292, 1986.
Dale et al, J Exp Med 158(5):1727–1732, 1983.
Fischetti V.A. Methods in Enzymology 235:286–294, 1994.
Van de Rijn et al, Infect Immun 32(1):86–91, 1981.
Kehoe MA, Vaccine 9(11):797–806, 1991.
Ish–Horowicz et al, "Rapid and efficient cosmid cloning" Nucleic Acids Research, vol. 9, No. 13, pp. 2989–2998, 1981.

*Primary Examiner*—James C. Housel
*Assistant Examiner*—Jennifer Shaver
*Attorney, Agent, or Firm*—Burns, Doane, Swecker & Mathis, L.L.P.

[57] ABSTRACT

Methods and compositions are provided for the cloning and expression of *Streptococcus pyogenes* M protein genes, and, in particular, types 5, 6 and 24 gene in single-cell host organisms. The streptococcal M protein produced by the recombinant DNA techniques described herein may be formulated for use as immunogens in vaccines to protect against *S. pyogenes* infections. The gene for the M protein may further be employed as a molecular probe for the accurate identification of streptococci in infected body tissues and fluids.

8 Claims, 4 Drawing Sheets

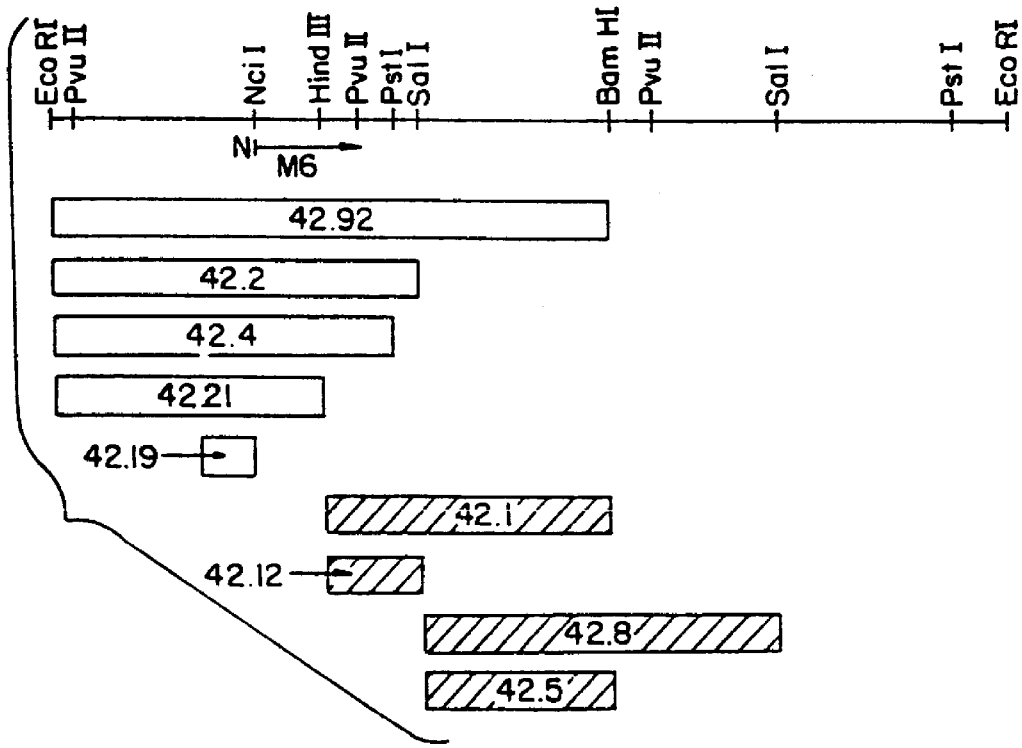

FIG. 3.

FIG. 4.

```
172 ATG BCT AAA AAT AAC ACS AAT AGA CAC TAT TCG CTT AGA AAA 213
    Met Ala Lys Asn Asn Thr Asn Arg His Tyr Ser Leu Arg Lys

214 TTA AAA AAA BGT ACT GCA TCA GTA GCA GTG GCT TTG AGT GTA 255
    Leu Lys Lys Gly Thr Ala Ser Val Ala Val Ala Leu Ser Val

256 ATA GGG BCA BGA TTA GTT GTC AAT ACT AAT GAA GTT AGT GCA 297
    Ile Gly Ala Gly Leu Val Val Asn Thr Asn Glu Val Ser Ala

298 AGA GTG TTT CCT AGG GGG ACG GTA GAA AAC CCG GAC AAA GCA 339
    Arg Val Phe Pro Arg Gly Thr Val Glu Asn Pro Asp Lys Ala
  N
340 CGA GAA CTT CTT AAC AAG TAT BAC GTA GAG AAC TCT ATG TTA 381
    Arg Glu Leu Leu Asn Lys Tyr Asp Val Glu Asn Ser Met Leu

382 CAA GCT AAT AAT GAC AAG TTA ACA ACT GAG AAT AAT AAC TTA 423
    Gln Ala Asn Asn Asp Lys Leu Thr Thr Glu Asn Asn Asn Leu

424 ACA GAT CAG AAT AAA AAC TTA ACA ACT GAG AAT AAA AAC TTA 465
    Thr Asp Gln Asn Lys Asn Leu Thr Thr Glu Asn Lys Asn Leu

466 ACA GAT C 472
    Thr Asp
```

PRODUCTION OF STREPTOCOCCAL M PROTEIN

This application is a continuation application of Ser. No. 08/061,812 filed on May 13, 1993, now abandoned, which is a continuation application of Ser. No. 07/800,890 filed on Nov. 27, 1991, now abandoned, which is a continuation application of Ser. No. 07/604,353 filed on Oct. 26, 1990, now abandoned, which is a continuation of Ser. No. 07/456,189 filed on Dec. 15, 1989, now abandoned, which is a continuation of Ser. No. 07/141,586 filed on Jan. 7, 1988, now abandoned, which is a divisional of Ser. No. 06/621,716 filed on Jun. 18, 1984, now U.S. Pat. No. 4,784,948 which is a continuation-in-part of Ser. No. 06/521,962, filed on Aug. 10, 1983, now abandoned.

The invention described herein was made in the course of work supported in part by grants from the National Institutes of Health of the Department of Health and Human Services.

1. FIELD OF THE INVENTION

This invention relates to compositions and processes for use as diagnostic probes and for the production of vaccines utilizing as an immunogen an antiphagocytic streptococcal protein, such as M6 protein of Group A streptococcus. The M protein is a fibrillar surface molecule which enables streptococcus to resist phagocytosis by macrophages and polymorpnonuclear neutrophiles of the infected host organism.

The present invention utilizes recombinant DNA techniques to insert a DNA sequence coding for M protein, or a portion thereof, into a DNA plasmid, such as viral DNA, plasmid DNA or cosmid DNA, such that the plasmid is capable of replicating and directing expression of the M protein gene in a bacterial host or other single cell system. The resulting recombinant DNA molecules are introduced into host cells to enable production of M protein, or a portion or molecular variant thereof. The protein produced is then isolated, purifies and modified for use as an immunogen in a vaccine against streptococcal infection.

This invention further provides a method for the detection of Group A, C and G streptococci. Such detection is achieved through the use of a specific molecular probe based on the entire gene or a segment of the gene coding for the M protein of Group A streptococcus. A DNA probe useful in a hybridization screening method is described herein for the examination of clinical isolates in cases of suspected streptococcal infection.

2. BACKGROUND OF THE INVENTION

It is well recognized that acute rheumatic fever and acute glomerulonephritis are sequelae of Group A streptococcal infection. In developing countries of the tropics and subtropics, rheumatic heart disease is currently the most common form of cardiac damage. Prevalence rates of this disease as high as 22–23 per thousand have been reported in school-age children in urban slums of some developing countries of the world. It is estimated that in India alone, as many as six million children may be afflicted. Although the exact mechanisms of disease causation are not understood, it is clear that rheumatic fever, as well as acute nephritis, follows infection with *Streptococcus pyogenes* (Group A streptococcus).

The streptococcal M protein is the major virulence factor of this bacterium by virtue of the fact that it imparts to the organism resistance to phagocytic attack. Antigenic variation is the primary mechanism by which the Group A streptococcus is able to evade the host's immune response and thus cause disease in man. Resistance to Group A streptococcal infection is dependent upon the presence of type-specific antibodies to the M protein, a fibrillar molecule found on the surface of the organism. In addition to a number of nontypable strains, about seventy distinct Group A streptococcal M types are currently recognized. Despite the fact that antibodies cross-reactive among certain M types are common, only antibodies prepared against the homologous type are capable of initiating phagocytosis of the organisms (i.e., are opsonic antibodies). Furthermore, not all homologous, or type-specific antibodies are opsonic.

The fact that specific antiserum can be prepared to Group A streptococci has made it possible to detect streptococcal infection by subjecting clinical isolates, such as those obtainable by throat swab, to serological testing. The identification of group A streptococci in an infection requires the isolation of the organism in pure culture, extraction of the group-specific carbohydrate, and reaction with group-specific antiserum. A clinical test for streptococcal infection that could be based upon a property common only to all pathogenic strains would thus be highly desirable.

2.1. RECOMBINANT DNA TECHNOLOGY AND GENE EXPRESSION

Recombinant DNA technology involves the technique of DNA cloning whereby a specific DNA fragment is inserted into a genetic element called a vector which is capable of replication and transcription in the host cell. The vector can be either a plasmid or a virus. Plasmids are small, circular molecules of double-stranded DNA that occur naturally in both bacteria and yeast, where they replicate as independent units as the host cell proliferates. These plasmids generally account for only a small fraction of the total host cell DNA, and often carry genes that confer resistance to antibiotics. These genes, and the relatively small size of the plasmid DNA, are exploited in recombinant DNA technology.

The inserted DNA fragment of a recombinant DNA molecule may be derived from an organism which does not exchange information in nature with the host organism, and may be wholly or partially synthetically made. Construction of recombinant DNA molecules using restriction enzymes and ligation methods to produce recombinant plasmids has been described in U.S. Pat. No. 4,237,224, issued to Cohen and Boyer. The recombinant plasmids thus produced are introduced and replicated in unicellular organisms by means of transformation. Because of the general applicability of the techniques described therein, U.S. Pat. No. 4,237,224 is hereby incorporated by reference into the present specification.

A different method for introducing recombinant DNA molecules into unicellular organisms is described by Collins and Hohn in U.S. Pat. No. 4,304,863 which is also incorporated herein by reference. This method utilizes a packaging/transduction system with bacteriophage vectors.

Because it is supercoiled, plasmid DNA can easily be separated from the DNA of the host cell and purified. For use as cloning vectors, such purified plasmid DNA molecules are cut with a restriction nuclease and then annealed to the DNA fragment that is to be cloned. The hybrid plasmid DNA molecules produced are then reintroduced into bacteria that have been made transiently permeable to macromolecules (competent). Only some of the treated cells will take up a plasmid and these cells can be selected for the antibiotic resistance conferred on them by the plasmid since they alone will grow in the presence of antibiotic. As these bacteria divide, the plasmid also replicates to produce a large number of copies of the original DNA fragment. At the end of the period of proliferation, the hybrid plasmid DNA molecules are purified and the copies of the original DNA fragments are excised by a second treatment with the same endonuclease.

Regardless of the method used for construction, the recombinant DNA molecule must be compatible with the host cell, i.e., capable of autonomous replication in the host cell. The recombinant DNA molecule should also have a marker function which allows the selection of host cells transformed by the recombinant DNA molecule. In addition, if all of the proper replication, transcription and translation signals are correctly arranged on the plasmid, the foreign gene will be properly expressed in the transformed cells and their progeny.

2.2. VACCINES

Vaccines are an approach to the control and prevention of diseases. Vaccines can be prepared by mixing the immunogenic portion of an antigen with an adjuvant. This preparation, when infected into a host animal or man, induces the production of antibody to the antigen, and thus provides active immunization to the disease caused by the relevant organism expressing the antigen.

Peptide vaccines contain only the necessary and relevant immunogenic material, such as portions of the surface proteins of bacteria and viruses. Peptide vaccines can be made by isolating the relevant peptide from a highly purified bacterial fraction, or by synthesizing the relevant polypeptide. A major advantage of peptide vaccines is the exclusion of unrelated material of bacterial origin and of host- or donor-derived interfering substances. However, at present, production of peptide vaccines using these methods is generally too expensive for widespread commercial use. Recombinant DNA technology has much to offer in the production of peptide vaccines; the molecular cloning and host cell expression of bacterial genes which encode the relevant immunogenic portions of the bacteria can produce sufficient quantities of the relevant immunogen for use in a peptide vaccine.

Vaccines are often administered in an emulsion with various adjuvants. The adjuvants aid in attaining a more durable and higher level of immunity using smaller amounts of antigen in fewer doses than if the immunogen were administered alone. The mechanism of adjuvant action is complex and not completely understood. However, it may involve the stimulation of phagocytosis and other activities of the reticuloendothelial system as well as a delayed release and degradation of the antigen. Examples of adjuvants include Freund's adjuvant (complete or incomplete), Adjuvant 65 (containing peanut oil, mannide monooleate and aluminum monostearate), and mineral gels such as aluminum hydroxide, aluminum phosphate, or alum. Freund's adjuvant is no longer used in vaccine formulations for humans or for food animals because it contains nonmetabolizable mineral oil and is a potential carcinogen; however, the mineral gels are widely used in commercial veterinary vaccines.

2.3. ATTEMPTS TO DEVELOP A STREPTOCOCCAL VACCINE USING M PROTEIN ANTIGEN

Fox, J. Immunol. 93:826–837 (1964) has used M proteins purified from streptococci as immunogens in rabbits to induce type-specific bactericidal antibodies. However, attempts at vaccinating humans with partially purified streptococcal M proteins have been met with varied success since strong local and systemic reactions usually occur in recipients. See Schmidt, J. Infect. Dis. 106:250–255 (1960) and Potter et al., J. Clin Invest. 41:301–310 (1962). Fox et al., J. Infect. Dis. 120:598–604 (1969) and Fox et al., J. Exp. Med. 124:1135–1151 (1966), using purified acid-extracted M protein, were partially successful with their vaccine. Of 22 adults vaccinated, 15 responded with a secondary rise in type-specific antibody titer; however, only 5 exhibited a rise in bactericidal antibodies.

Beachey et al., J. Exp. Med. 150:862–877 (1979) vaccinated 12 adults with an alum precipitated preparation of a pepsin-derived fragment of the M24 protein (Pep M24). This was considered well tolerated since no local or systemic reactions were observed. Ten of the 12 persons vaccinated responded by developing M24 type-specific opsonic antibodies.

Immunological studies by Dale et al., J. Exp. Med. 151:1026–1037 (1980) revealed that 2 of the 12 volunteers, though immunized with M24, also developed antibodies that bind to both M5 and M6 proteins, of which only the M6 was opsonic. However, Beachy et al., in Symposium on Bacterial Vaccine, Ed. J. B. Robbins, J. C. Hill, Brian Decker Publisher, New York, pages 401–410 (1981), found that of four rabbits immunized with purified Pep M5 protein (pepsin-derived fragment of the M5 protein), one produced antibodies directed against cardiac tissue in high titer. This antisera cross-immunoreacted with type M5 protein and cardiac tissues.

2.4. DNA HYBRIDIZATION ASSAYS

A general diagnostic method for the detection of pathogenic microorganisms may be devised if a DNA segment of the genome expected to be found in such organisms is available in pure form. If it is, the DNA segment may be used as a hybridization probe, by tagging it with a chemical, enzymatic or radioisotopic reporter group.

Grunstein and Hogness [Proc. Natl. Acad. Sci. U.S.A. 72:3961 (1975)] have used this approach in a method called colony hybridization, where bacteria to be assayed were transferred to a nitrocellulose filter. The colonies on the filter were then lysed, and the genomic DNA released was fixed to the filter. The presence of nucleotide sequences in the affixed DNA that were complementary to the sequence of a $^{32}$P-labeled probe was then monitored by autoradiography. Other general aspects of DNA hybridization have been described by Falkow et al. in U.S. Pat. No. 4,358,535.

3. SUMMARY OF THE INVENTION

Methods and compositions are provided for the cloning and expression of the streptococcal M protein gene in single cell organisms. Also described are methods for culturing these novel single-cell organisms to produce M protein, a rapid assay for identifying single colonies which express the M protein DNA, and a method for identification of the gene product. The M protein produced by the recombinant DNA techniques described herein may be formulated for use as an immunogen in a vaccine to protect against *Streptococcus pyogenes* infection.

In a particular embodiment disclosed herein, the protein produced by *E. coli* transductants is slightly larger than the M6 protein isolated by solubilization of the Group A streptococcal cell wall, but similar in size to that secreted by streptococcal protoplasts and L-forms. Immunologically, the molecule synthesized by *E. coli* transductants has the same type-specific determinants as the streptococcal M6 protein. The M protein was characterized antigenically by Ouchterlony double diffusion experiments and immunogenically by (a) an opsonic antibody removal test and (b) ability to elicit production of opsonic antibodies. The cloned M protein was isolated and then sized by sodium dodecyl sulfate polyacrylamide gel electrophoresis. Additionally, methods are described for isolating the expressed gene product.

The present invention provides a method of producing streptococcal opsonic antibodies and antigens of general importance in human medicine and in microbiological research. This includes use of streptococcal M proteins produced by the present invention as highly reproducible standard antigens for ultrasensitive assays such as radioimmunoassays. These assays may be used as diagnostic tools for detection of antibodies to streptococcus in biological samples.

Through the use of the streptococcal M protein gene or a fragment thereof as a molecular probe, a method is also provided for the diagnostic identification of pathogenic streptococci in body tissues and fluids. In this method, DNA is extracted from microbial isolates and examined for complementary nucleotide sequences by hybridization to the molecular probe. By this means large numbers of isolates may be screened for the presence of streptococci with relative ease, high sensitivity and accuracy. The result is a screening test offering marked advantages over the more cumbersome serological diagnostic tests presently in use.

4. BRIEF DESCRIPTION OF THE FIGURES

The present invention may be more fully understood by reference to the following detailed description of the invention and the figures in which:

FIG. 1 (not to scale) represents the construction of pJRS42, a recombinant plasmid derived from streptococcal DNA fragments and pJB8. (See Section 6.2. ) Various restriction sites within the streptococcal DNA are not shown.

Figure 2:
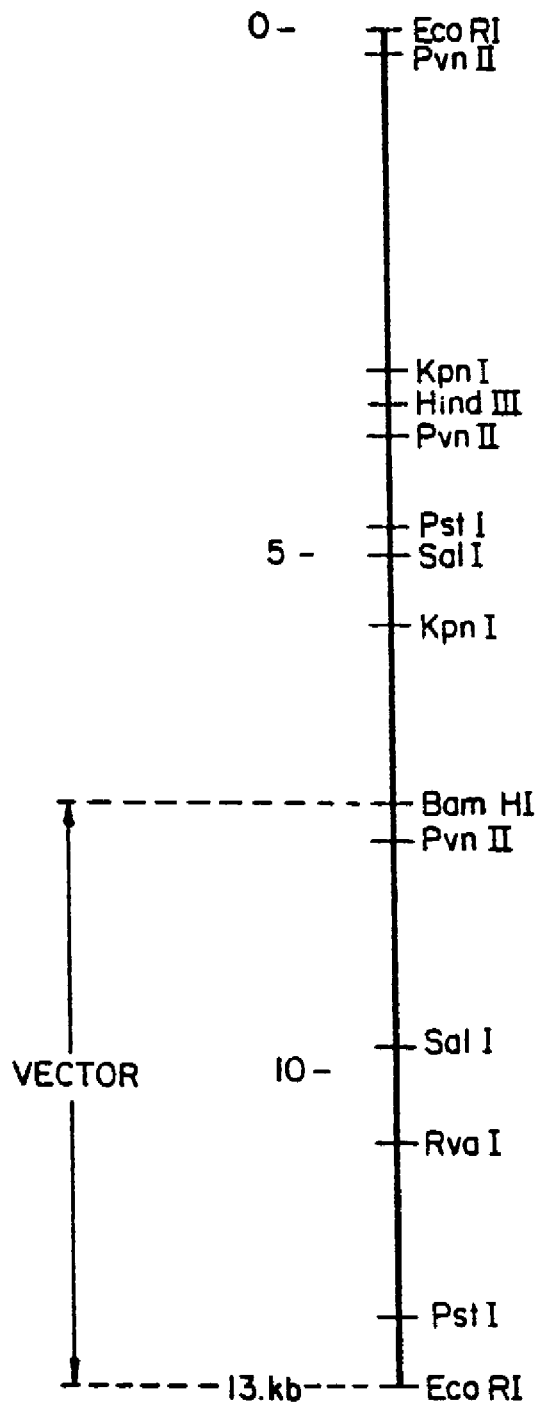

FIG. 2 represents a restriction map of pJRS42.13. This plasmid was derived from pJRS42 by digestion with EcoRI to remove unnecessary streptococcal DNA, then religated. Plasmid pJRS42.13 has only a single EcoRI site. (See Section 6.3. )

FIG. 3 is a restriction map of various subclones of plasmid pJRS42.13, which contains the genes coding for the M6 protein of type 6 Group A streptococcus. The clear boxes define clones that express M6 protein, and the shaded boxes denote clones that do not. The vector pBR322 was used in all cases except 42.21 and 42.19, which are in M13 and in pUC8 and pUC9, respectively. The arrow above the restriction map indicates the direction of transcription of the gene encoding type 6M protein (emm6), and the approximate extent of the gene. The end of the molecule corresponding to the amino terminus of the protein is denoted by "N".

FIG. 4 is a representation of a portion or the DNA sequence of the emm6 gene that encodes the amino terminal end of the M6 protein, as determined by the method of Sanger et al. [Proc. Natl. Acad. Sci. U.S.A. 74: 5463 (1977)], and the amino acid sequence of the protein as predicted from the DNA sequence. The amino terminal amino acid, as determined by sequential Edman degradation (reference), is indicated by an "N" below the amino acid sequence.

Figure 5:
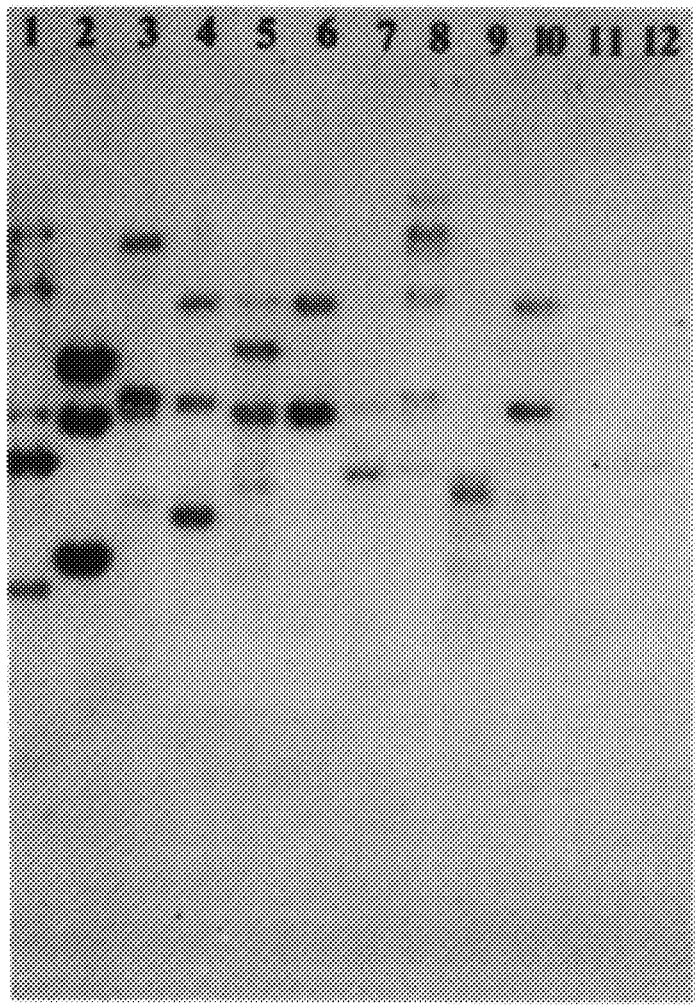

FIG. 5 represents agar gel electrophoretic analysis of DNA hybridization with the NciI/PvuII emm6 DNA probe from the restriction enzyme digestion of plasmid pJRS42.13 of FIG. 3. The DNA in each lane is as follows: lane-l, oligonucleotide size standards of 10.90, 7.74, 5.15, 2.44, 1.80 and 0.60 kb; lane 2, M6 strain D471; lane 3, M47; lane 4, M5; lane 5, M19; lane 6, M26; lane 7, M11; lane 8, M24; lane 9, M12; lane 10, M23; lane 11, M28 (from M-strain T28/51/4); and lane 12, M28 (from M+ strain T28/150A/5).

5. DETAILED DESCRIPTION OF THE INVENTION

5.1. M PROTEIN IMMUNOGENS

This invention relates to the use of recombinant DNA techniques to produce streptococcal M proteins which can be used as immunogens in vaccine formulations. More specifically, the production of M6 protein is described.

The recombinant plasmids, constructed as described herein, provide for host cell (procaryotic or eucaryotic) production of a streptococcal h protein which is stable and resistant to host cell degradation. Such plasmids enable the generation of large quantities of protein, or a fragment thereof, containing immunological and antigenic determinants of naturally-occurring M protein. The particular embodiment described herein concerns M6 protein. However, the DNA molecules described herein are not limited to the production of M6 protein and may be used to produce any of the Group A streptococcal M proteins.

Generic applicability to all M proteins of the compositions and methods disclosed herein for M6 protein is apparent from the research of Fischetti and manjula (1982, Biologic and Immunologic Implications of the Structural Relationship Between Streptococcal M Protein and Mammalian Tropomyosin, pp. 411–448 in Robbins, Hill and Sadoff (eds.), Bacterial Vaccines). For example, all of the M proteins sequenced so far, including M5, M6 and M24, exhibit significant homology and all are coiled-coil structures. The amino terminal and other sequenced segments of the three M molecules reveal that they all exhibit a repeating seven-residue periodicity. Additionally, immunologic analysis of several M types has revealed cross-reactions among various types. Fischetti, J. Exptl. Med. 146:1108–1123 (1977); Manjula and Fischetti, J. Exptl. Med. 151:695–708 (1980); Manjula and Fischetti, J. Immunol. 124:261–267 (1980). Furthermore, the hybridization data presented below indicates structural similarity among all 56M protein genes tested.

It can readily be seen by those skilled in the art that various immunogens and vaccine formulations can be prepared.

5.2. M PROTEIN MOLECULAR PROBE

The M protein gene described herein, or a fragment thereof, may be used as d molecular probe in a diagnostic test for streptococci. The basis of the test is the fact that pathogenic streptococci possess gene sequences that are complementary to segments of the M protein gene of this invention. Such gene complementarity may be readily detected by isolating microbial DNA from a suspected streptococcal infection and annealing the DNA with the molecular probe under appropriate conditions on a solid support or in liquid medium. The occurrence of hybridization may readily be detected by attachment to the probe of a suitable reporter group.

Streptococcal organisms might be isolated from a point of infection in any body tissue or fluid, but a simple throat swab would be the most likely source. The microorganisms thereby obtained, which would probably be a mixed culture, can be used directly (e.g., on the swab) or grown first to produce more cells in any of the culture media that are well known to those skilled in the art. Then, the DNA from the mixed culture can be extracted, following disruption by freeze-thawing, sonication or other mechanical means and/ or by treatment with general or specific agents that lyse bacterial cell walls.

The extracted DNA is generally denatured by the addition of aqueous alkali and then washed with a buffered solution. The particular concentrations of alkali, buffer constituents, etc., depend on the conditions of the experiment and may be readily determined by routine experimentation. The denatured M protein gene probe of this invention may then be added to the microbial DNA preparation and permitted to hybridize at points of DNA sequence complementarity. Specific binding will be recognized as that remaining after extensive washing of the hybridization mixture to eliminate non-specific binding.

The hybridization may be carried out in one of numerous solutions that have been developed and are acceptable for the purpose. Falkow et al. have described many of the considerations of solution composition and the hybridization process in general in U.S. Pat. No. 4,358,535, which because of its general utility is hereby incorporated by reference. The specific values of other hybridization parameters, such as time and temperature, and the method employed are not essential to this invention. Methods described by Gall and Pardue [Proc. Natl. Acad. Sci. U.S.A. 63:376–383 (1969)] and by John et al. [Nature 223:582–587 (1969)], for example, can be applied. Indeed, it is expected that the method of choice for hybridization will change as the state of that art advances.

The molecular probe upon which the present invention is based may encompass all or only a portion of the M protein gene, as long as enough of the gene sequence is retained to permit specific hybridization to occur. Such hybridization may be detected even at extremely low levels by coupling an appropriate reporter group to the molecular probe. The probe may be radiolabeled (e.g. labeled with $^{32}P$, $^{3}H$, $^{14}C$, $^{35}S$ etc.), or it may be tagged with a chemical or enzymatic reporter group. For example, colorimetric detectors coupled to biotinylated probes may be used in conjunction with avidin derivatives such as fluorescein-avidin, rhodamine-avidin, or enzyme-linked avidin.

The following Example of a method for the cloning and expression of the M6 protein in *Escherichia coil* and for the use of the M6 protein gene as a probe to characterize streptococcal infection is given for purposes of illustration and not by way of limitation on the scope of the invention.

6. EXAMPLE

PREPARATION OF THE CLONE CONTAINING THE STREPTOCOCCAL M PROTEIN GENE, AND USE OF THE GENE AS A MOLECULAR PROBE IN A DIAGNOSTIC TEST FOR STREPTOCOCCAL INFECTION

6.1. ISOLATION OF STREPTOCOCCAL DNA

The source of the M6 protein gene was *Streptococcus pyogenes* strain D471 (Group A streptococcus). Group C streptococcal phage lysin, in the presence of 30% raffinose, was used to solubilize the Group A streptococcal cell wall leaving stable protoplasts (Phillips et al., Proc. Natl. Acad. Sci., U.S.A. 78:4689 (1981)). The protoplasts were then washed extensively and treated with proteinase K to remove streptococcal DNAse. Protoplasts were lysed by dilution into sodium dodecyl sulfate (SDS) and the extract was treated with ribonuclease I to digest RNA. Cesium chloride was added. The preparation was centrifuged at about 100×g to remove protein and dialyzed overnight. The DNA was precipitated with ethanol. The DNA fragments which were selected for use were well over 100 kilobases (kb) before digestion (as assayed by agarose gel electrophoresis on a 0.4% agarose gel with P1 phage DNA as a 100 kb standard and one-half P1 molecules as a 50 kb standard).

6.2. CLONING INTO E. COLI

A large piece of streptococcal DNA was to be cloned in order to reduce the number of candidate *E. coli* clones that needed to be screened for M protein production and to retain regulatory regions associated with the structural gene for M protein. Therefore, a cosmid vector that accepted DNA insertions of 35–40 kb was necessary. The 5.4 kb vector, pJB8, was chosen as the cloning vehicle. This vector had been constructed from the ampicillin resistant plasmid HomerI and a synthetic BamHI linker in the manner described by Ish-Horowitz and Burke, Nucleic Acids Res. 9(13) :2989–2998 (191).

In the present invention, vector pJB8 was digested with BamHI as generally described by Maniatis et al., supra, pp. 104–106) which cleaves the vector at a unique site to generate "cohesive ends". The cleaved vector was treated with alkaline phosphatase (e.g., as in Maniatis, et al., supra, 133–134) to remove the 5'-phosphates of the linearized vector in order to prevent vector-vector religation and recircularization. To generate random DNA fragments, Sau3a restriction enzyme was used to partially digest the streptococcal DNA (e.g., as in Maniatis, et al., supra, 298) isolated as described in Section 6.1. The fragmented streptococcal DNA was ligated into the BamHI site on the pJB8 vector (see FIG. 1, e.g., as in Maniatis, et al., supra, 298–299).

The vector with streptococcal DNA inserted was packaged into lambda phage heads in vitro [see Hohn and Collins, Gene 11:291 (1980)]. The phage containing packaged chimeric DNA was used to transduce the *E. coli* K12 restriction-less strain C600NR(lambdacI857)recA which carries a thermally inducible prophage. Ampicillin resistant colonies were selected at 30° C., transferred to the same selective medium and incubated at 30° C. overnight to provide a master plate.

The possibility that the M protein gene would be expressed in *E. coli* was high because most gram positive genes that have been cloned in *E. coli* have been expressed. However, it was unlikely that the M protein would appear on the surface of *E. coli* since it would have to be transported through the periplasm and the outer membrane, neither of which exist in streptococcus. For that reason, the *E. coli* master plate was then shifted to 42° C. to induce prophage and lyse the host cells to detect expression of the cloned gene. [Shalka and Shapiro, Gene 1:65 (1976)]

6.3. RAPID ASSAY OF SINGLE COLONIES FOR EXPRESSION OF M PROTEIN

A rapid assay was developed to recognize the clone of *E. coli* expressing M protein. This technique readily distinguished single colonies expressing M protein.

The assay involved transferring the lysed colonies to be tested to nitrocellulose filters, rinsing the filters in bovine serum albumin to reduce non-specific affinity of the filter for proteins, reacting the filter with antiserum to purified LysM6 that had been exhaustively pre-absorbed with *E. coli* cells, rinsing appropriately, reacting with $^{125}$I-Staphylococcal protein A (which binds to the antigen-antibody complexes), rinsing again, and scoring by autoradioyraphy.

To detect the M6 protein, the antiserum was diluted over 1000-fold. There was no detectable reaction with *E. coli* when the antiserums was used at a 10-fold dilution (over 100 times more concentrated). By this method, production by an *E. coli* clone of less than 1% of the amount of M6 protein produced in the parental streptococcus was detectable.

Among 335 colonies screened, one reacted strongly with antiserum to purified M6 protein. The chimeric plasmid present in this strain was named pJRS42. The ability of this *E. coli* clone to produce the M6 protein was stably maintained on subculture in ampicillin-containing medium.

Plasmid pJRS42 was treated with EcoRI endonuclease which led to removal of a segment of streptococcal DNA to form pJRS42.13. This plasmid retained all necessary replication functions and the entire sequence coding for the M6 protein with its promoter system.

6.4. IDENTIFICATION OF THE GENE PRODUCT

*E. coli* strain C600NR containing pJB8 and C600NR transductant containing pJRS42 were grown at 30° C. to late log phase in Todd-Hewitt broth (beef heart infusion broth) containing ampicillin. The cells were pelleted and washed twice, and lysed with ethylene diaminetetraacetic acid (EDTA)-lysozyme followed by freezing in dry ice-ethanol and thawing quickly at 37° C. Following treatment with DNAse, the cellular debris was removed by centrifugation at 10,000×g for 30 minutes and the extract was passed through a 0.45 micron Millipore filter and dialyzed against 50 mM ammonium bicarbonate.

The identification of M protein molecule produced in *E. coli* was determined by immunoblot analysis. Equivalent protein concentrations, as determined by the Folin reaction [Lowry et al., J. Biol. Chem. 193:265 (1951)], were applied to a 12% polyacrylamide gel containing SDS. A standard preparation of purified M6 protein extracted from the type 6 streptococcus by solubilization of the cell wall with phage lysin was applied to an adjacent well as control. After electrophoresis, the separated proteins were transferred to nitrocellulose and unreacted sites on the filter were blocked using Tween 20 (polyoxyethylene sorbitan monolaurate), and the filter was incubated with antiserum directed against M6 protein extracted by lysin from streptococcus that had been absorbed with *E. coli*. An enzyme-linked immunoassay using alkaline phosphatase conjugated to goat anti-rabbit IgG was used to detect the bound antibody. Bands were visualized using indoxyl phosphate as the alkaline phosphatase substrate and nitroblue tetrazolium as the chromophore by the method of Blake et al. [anal. Biochem. 136:175–179 (1984)]. The M6 antiserum reacted with both the M6 control and the extract of the *E. coli* clone containing pJRS42, but not with the extract from the parent *E. coli* strain containing only the pJB8 vector.

The molecular weight of the M protein produced by the *E. coli* clone was compared by immunoblot analysis to a standard preparation of purified LysM6 protein. This molecule is the result of solubilization of the cell wall of the streptococcus with the enzyme phage lysin and purification by column chromatography. It represents the largest M protein molecule isolated from the streptococcal cell wall.

The M6 protein was purified as follows: The *E. coli* containing plasmid pJRS42.13 was treated with lysozyme in the presence of EDTA and 20% sucrose. This allowed the periplasmic contents to be released into the surrounding fluid. Centrifugation of the organisms left the periplasmic contents in the supernatant along with other *E. coli* associated proteins. Using this technique it was found that the M protein was in high concentration in the periplasmic space and virtually absent from the cytoplasm. Thus, this method was used to generate the starting material for the M protein purification.

The M protein in the crude periplasmic contents was purified from other contaminating proteins by column chromatography. The crude periplasmic preparation was dialyzed against 5 mM ammonium bicarbonate buffer pH 5.5 and applied to a column of carboxymethyl cellulose. The column was washed with three volumes of the same buffer and the adherent proteins eluted in one step with 100 mM sodium phosphate pH 7.0. The eluted protein (containing the M protein) was applied directly to a hydroxylapatite column equilibrated in 25 mM sodium phosphate pH 7.0.The column was washed with 2 column volumes of 200 mM sodium phosphate pH 7.0 and the adherent M protein was then eluted with 400 mM sodium phosphate pH 7.0. This method resulted in a highly purified M protein preparation as determined by SDS-polyacrylamide gel electrophoresis and sequence analysis.

Amino terminal sequence analysis of the purified coli-synthesized M6 protein yielded a single phenylthiohydantoin (PTH)-amino acid at each degradation step, verifying the homogeneity or the final preparation. In addition, the amino terminal sequence was found to be identical to that of the LysM6 molecule through the first 35 residues sequenced, with the exception of the amino terminal residue. The *E. coli* molecule has an additional arginine residue at the amino terminus which may be clipped off during purification of the lysine molecule.

The purified LysM6 preparation exhibited a multiple banding pattern previously observed with the M6 molecule, which is probably due to degradation during extraction and purification. The three major bands corresponded to apparent molecular weights of 51,000, 52,000 and 53,000 daltons. The size heterogeneity of the M6 preparation probably resulted from differences at the carboxy-terminal region of the protein since, during amino terminal sequence analysis of this preparation by sequential degradation, only a single amino acid residue was released at each step. Since the bands from the pJRS42-containing clone that reacted with anti-M6 antibodies are all larger (molecular weights 55,000, 57,000, 59,000 daltons) than any from the streptococcal preparation, this suggested that pJRS42 contained the entire structural gene for the M6 protein. This was supported by the fact that this molecular size correlated well with the reported size of M protein secreted from protoplasts and L forms of type 12 streptococci (molecular weight 58,000 daltons). Thus, the proteins in the *E. coli* preparation may be closer to the size of the intact native M molecule than those released by lysin-extraction of streptococcus.

In addition, the M protein isolated from secreting streptococcal L forms and protoplasts appeared more homogeneous. There are several possible explanations for the differences in mobilities of the *E. coli* protein(s) reactive with anti-M6 antibodies from those of the bands of the purified standard M protein. For example: 1) The protein(s) may include a leader sequence that has not been removed in the *E. coli* but is normally removed in streptococci; 2) the LysM6 molecule may represent a cleavage product produced during attachment to the streptococcal cell wall; 3) the LysM6 molecule may be a partial degradation product produced during purification of the protein; 4) the *E. coli* protein(s) may be a "fusion" product produced from a promoter in the vector; 5) a weak translational start sequence that is unable to function in streptococcus may be active in *E. coli*; and/or 6) the "stop" condon normally functional in streptococcus may be suppressed by the supE mutation in the *E. coli* strain.

6.5. IMMUNOGENIC CHARACTERIZATION OF THE GENE PRODUCT

An Ochterlony immunodiffusion comparison of M protein of *E. coli* with that extracted by lysin from streptococcus was performed. Well 1 contained unabsorbed rabbit antiserum prepared against lysin-extracted M6 protein synthesized by the streptococcus; Well 2 contained purified lysin-extracted M6 protein; Well 3 contained M6 protein from the *E. coli* strain C600NR (pJRS42) which had been partially purified by chromatography on DEAE and CM cellulose. The reaction was performed in 1% agar gel prepared at pH 8.6 in 50 mM barbitol buffer. The gel was dried and stained with Coomasie blue.

The results of this double diffusion experiments (gel not shown) supported the conclusion that the extract of the *E. coli* carrying pJRS42 (but not that of the plasmid without insert) contained a molecule with antigenic determinants common to at least some of those of streptococcal M6 protein. Thus, the M6 protein synthesized in *E. coli* has at least some of the same type-specific determinants as the M protein extracted from type 6 streptococci, although the *E. coli* product has a higher apparent molecular weight.

6.6. BACTERICIDAL EFFECT OF CLONED M PROTEIN

In order to determine if the M protein produced by the *E. coli* contained the antigenic determinants necessary to remove opsonic antibodies from both rabbit and human opsonic antiserum, the following absorption experiment was performed.

Purified *E. coli* -synthesized M6 protein was lyophilized in two 30 μg aliquots. Rabbit type 6 opsonic antiserum (0.5 ml) was added to one, and a similar amount of human serum opsonic for type 6 streptococci was added to the other dried protein sample to form a solution. The tubes were incubated at 37° C. for one hour and allowed to remain at 4° C. overnight. The precipitate that formed was centrifuged at 20,000×g and the resulting supernatant was used in a bactericidal assay using type 6 streptococci.

The indirect bactericidal assay was carried out as described originally by Lancefield, J. Exptl. Med. 110:271 (1959). Heparinized whole human blood from normal donors was used as a source of phagocytes. Dilutions of type 6 streptococci (100 μl) were mixed with 400 μl of the human blood in the presence or absence of either absorbed or unabsorbed serum (100 μl ). The mixture was rotated end over end at 37° C. for 3 hr. The surviving organisms were determined by pour plate method. Rotated controls without antiserum were run to test the ability of the streptococci to grow in the donor's blood.

The M protein produced by *E. coli* transductants removed the opsonic antibodies from both the rabbit and human sera. See Table 1. Thus, the anti-phagocytic determinants of the *E. coli* M protein function similarly to those of the native M6 molecule.

TABLE 1

REMOVAL OF HUMAN AND RABBIT OPSONIC ANTIBODIES WITH *E. COLI* PRODUCED M6 PROTEIN

| | Colonies Found* | |
|---|---|---|
| Treatment | Rabbit anti-M6 | Human anti-M6 |
| Inoculum | 20 | 18 |
| No serum (control) | 790 | 930 |
| Unabsorbed serum | 8 | 0 |
| Absorbed with *E. coli* M6 | 1800 | 2890 |

*Numbers represent colony forming units as assayed by pour plate method after the 3 hour rotation.

6.7. PRODUCTION OF TYPE 6 OPSONIC ANTIBODIES

Production of type 6 opsonic antibodies in rabbits after immunization with purified *E. coli* -produced M6 protein was accomplished as follows. Antisera to the purified *E. coli*-produced M6 protein was prepared in New Zealand white rabbits. The primary inoculation consisted of 100 μg of M6 protein emulsified with complete Freund's adjuvant and given subcutaneously at multiple sites. The animals were boosted after 4 weeks with the same dose of the M6 protein in incomplete Freund's adjuvant. Animals were bled 10 days later.

As determined by bactericidal assay (described above), rabbits immunized with the *E. coli* M6 protein developed antibodies which allowed phagocytosis of type 6 streptococci. See Table 2.

TABLE 2

PRODUCTION OF OPSONIC ANTIBODIES IN RABBITS IMMUNIZED WITH COLI M6 PROTEIN

| | Colonies* |
|---|---|
| Inoculum | 43 |
| No serum (control) | 1112 |
| Immune serum | 0 |

*Protocol is that described in Section 6.6., supra. Numbers represent colony forming units as assayed by pour plate method after the 3 hour rotation.

6.8. DIAGNOSTIC TEST FOR STREPTOCOCCI

6.8.1. PREPARATION AND PURIFICATION OF AN M-GENE DNA PROBE

To locate the gene encoding type M6 protein (emm6), plasmid pJRS42.13, described in Section 6.3, supra, as subjected to digestion with various restriction enzymes or combinations of them. The DNA fragments thus obtained were sized by electrophoresis through 0.8% agarose gel as described by Maniatis, et al., supra, 150–161, and then ligated into different vectors. These recombinant vectors were transformed into an *E. coli* K12 bacterium that was lysogenic for a thermally inducible lambda prophage and screened for the production of protein reactive with anti-M6 protein antiserum, as described in Section 6.4.

The results of M6 protein expression analysis for many of these cloned DNA fragments are shown in FIG. 3. The clones delineated by clear blocks produced a protein that was reactive with anti-M6 antiserum, while those shown as shaded blocks did not. Although some of the reactive clones such as pJRS42.19 contained too little streptococcal DNA to encode the entire M6 protein, their expression products were evidently of sufficient size to show antigenic reactivity with the polyclonal antiserum.

To learn more about the orientation of the emm6 gene within the cloned DNA fragments, the streptococcal DNA in plasmid pJRS42.19 was ligated into the BamHI sites of plasmids pUC9 and pUC8 [Messing and Veira, Gene 19:269–276 (1982)]. The relationship of these plasmids to each other is such that inserted DNA is arranged in opposite orientations in the plasmids. Anti-M6 antiserum reacts with the products of both of these clones, indicating that the M6 protein fragment is synthesized when the streptococcal DNA is present in either orientation in these vectors. It thus appears that the inserted streptococcal DNA carries its own promotor. It this conclusion is correct, pJRS42.19 should encode the N-terminus of the M6 protein.

Following ligation of the streptococcal DNA fragment of pJRS42.19 into M13mp8 and mp9 [Messing and Veira, supra], the sequence of the inserted DNA was determined by the Sanger dideoxy method [Sanger et al., Proc. Natl. Acad. Sci. U.S.A. 74:5463 (1977)]. The portion of the sequence encoding the amino terminal end of the M6 protein, together with the amino acid sequence specified by it, is shown in FIG. 4. The amino terminal amino acid, as determined by sequential Edman degradation (reference), is indicated by an "N" below the amino acid sequence. The amino acid sequence determined in this way was identical to that established for the amino terminus of M6 protein that had been extracted either by pepsin treatment or by phage lysis from streptococcal strain D471 [reference]. It was also identical to the amino terminal region of the M protein produced by recombinant DNA methodology in E. coli in Section 6.4, supra.

These results showed that the emm6 gene begins within the DNA fragment contained in pJRS42.19. Comparison of the DNA sequence with the amino acid sequence shown in FIG. 4 further demonstrates that the N-terminus of M6 protein is at a point that is 32 bases to the left of the Nci I site, as shown in FIG. 3.

The M6 protein produced in E. coli was shown by sodium dodecyl sulfate polyacrylamide gel electrophoresis [Fischetti et al., J. Exptl. Med. 159:1083–1095 (1984)] to have an apparent molecular weight of 59,000 daltons. This fact would place the other end of the gene sequence at or near the PvuII site in FIG. 3. Further sequence analysis revealed that the nonsense codon terminating the protein, TAA, is located 38 bases to the right of the PvuII site (Hollingshead et al., manuscript in preparation).

A suitable probe containing a large portion of the emm6 gene was prepared by treating plasmid pJRS42.13 with NciI and PvuII. The location of this probe within the pJRS42.13 restriction map is indicated by the heavy arrow in FIG. 3. This probe fragment was purified by electrophoresis in 0.8% agarose gel, electroeluted, and passed through an Elutip-d column (Schleicher and Schuell) 6.8.2. ISOLATION OF BACTERIAL DNA Phage lysin was used to lyse cells of Group A streptococci, by the method of Fischetti et al. [J. Exptl. Med. 133:1105 (1971)]. For other streptococci, overnight Todd-Hewitt-yeast broth cultures (beef heart infusion broth with yeast extract) were diluted ten-fold and grown at 37° C. to a cell concentration of about $5 \times 10^6$ cells per ml. Glycine was added to a concentration of 3% (w/v), and the cells were incubated for 2 additional hours at 37° C. The cells were then washed, sonicated twice for 15-second pulses, and resuspended in 10 mM Tris-HCl buffer (pH 8.0) containing 30% (w/v) sucrose and 10 mg/ml lysozyme.

After incubation for 30 minutes at 37° C., ethylenediaminetetraacetic acid was added to a final concentration of 10 mM, and incubation was continued for an additional 30 minutes at 37° C. Protease K (0.1 mg/ml, source) and sodium dodecyl sulfate (1% w/v) were then added, the components were mixed by gentle inversion, and incubation was continued for another 30 minutes at 37° C. Following this procedure the cell suspensions, which displayed no turbidity, were extracted with phenol:chloroform (10:1) until no protein was visible at the interface. The extracted DNA was then precipitated with ethanol.

The bacterial strains examined include Staphylococcus aureus, B. subtilis (strain CU1065) Streptococcus pneumoniae and the following streptococcal strains from The Rockefeller University collection that are standard typing and grouping strains, respectively, used to prepare specific antisera: M1, T1/195/2; M3, B930/61/5; M3R, D58X; M4, T4/95/RB5; M5, T5B/126/4;M6, S43/192/3; M8, C256/86/3; M11, T11/137/3; M12, T12/126/4 (COL 6); M14, T14/46/8; M15, T15/23/7; M18, J17C/55/4; M22, T22/146/1; M23, T23/102/RB5; M24, C98/135/2; M25, B346/136/1; M27, T27/87/1; M28, T28/150A/5; M29, D23; M30, D24/126/3; M31, J137/69/3; M32, C121/39/8; M33, C107/102/2; M36, C119/83/2; M37, C242; M38, C94/80/2; M39, C95/95/1; M40, C143/25/9; M41, C101/103/4; M42, C113/55/5; M43, C126/170/2; M46, C105/41/5; M47, C744/RB4/6/5; M48, B403/48/5; M49, B737/137/2; M50, B514/33/6; M51, A309/77/1; M52, A871/106/2; M53, A952/94/3; M54, A953/87/3; M55, A928/73/1; M56, A963; M57, A995/91/2; M58, D315/87/3; M60, D335/38/3; M63, D459/50/2; M66, D794/76/2; M67, D795/95/1; group A, J17A4; group B, 090R; group C, C74; group D, D76; group E, K131; group F, F68C; group G, D166B; group H, F90A; group L, D167A; group M, D168A"X"; group N, C559; group O, B361. The following group A M typing strains from the Center for Disease Control, Atlanta, Ga., were also used: M2, SS633; M9, SS754; M13, SS936; M17, SS631; M19, SS400; M34, SS134; M59, SS913 and M62, SS984.

6.8.3. DOT BLOT HYBRIDIZATION STUDIES

Dot hybridization was performed on the extracted DNA samples using the procedure for detection of specific DNA sequences described by Kafatos et al. [Nucleic Acid Res. 7; 1541–1552 (1979)]. For a probe, the NciI/PvuII DNA fragment containing most of the emm6 gene (Section 6.8.1) was used following labeling with $^{32}P$ by nick translation by the method of Botchan et al. [Cell 9: 269–287 (1976)].

To carry out the hybridization, the DNA extracts from the various microbial sources were denatured in 0.6N NaOH for 15 minutes at room temperature, and then for 10 minutes at 0° C. Then, the samples were neutralized with 2M ammonium acetate, and aliquots of the DNas were spotted on Biodyne A 0.2 micron nylon filters (Pall Filtration Corp., Glen Cove, N.Y.) in a Bethesda Research Laboratories manifold. Hybridization was carried out by adding at least $2 \times 10^6$ cpm/filter of the nick-translated $^{32}P$ probe in buffer containing 1.8M Tris-HCl with 0.2M Tris base, and the filters were maintained at 64° C. overnight. The filters were then washed 10 times with the same buffer at 64° C., dried, and subjected to autoradiography on Kodak XAR-5 film with an intensifying screen. The exposure was carried out at −80° C. for 2–4 days.

A summary of the results of these studies is shown in Table 3.

TABLE 3

DNA HYBRIDIZATION WITH THE emm6 PROBE

| Bacterial Type | Strains Showing Hybridization | Strains Showing No Hybridization |
|---|---|---|
| Group A | 1, 2, 3, 4, 5, 6, 8, 9, 11, 12, 13, 14, 15, 17, 18, 19, 22, 23, 24, 25, 27, 28, 29, 30, 31, 32, 33, 34, 36, 37, 38, 39, 40, 41, 42, 43, 46, 47, 48, 49, 50, 51, 52, 53, 54, 55, 56, 57, 58, 59, 60, 62, 63, 66, 67, 68, A486, A712, D366, D780 | |
| M⁻ Group A Strains | J17A4, *A486 Var. | T28/51/4 |
| Other Streptococcal Groups | C, G | B, D, E, F, H, L, M, N, O |
| Other Gram Positive Organisms | None | *Streptococcus pneumoniae* *Staphylococcus aureus* *Bacillus subtilis* |

*Strain A486 Var. is a group A variant strain.

Overall, the dot blot test showed hybridization between the emm6 probe and DNA from 56/56 different M types of group A streptococcus, and from 4 non-typable group A strains and from 2 strains previously characterized as M⁻. No hybridization was seen with DNA from the gram positive organisms *Staphylococcus aureus* or *Bacillus subtilis*, from streptococcal Lancefield groups B, D, E, F, H, L, M, N or O, or from *Streptococcus pneumoniae*. Hybridization was observed, however, with groups C and G streptococcal DNA. This finding was not unexpected since group C streptococci have occasionally been implicated in human infections, and some strains appear to have a molecule on their outer surfaces which is functionally similar to M protein [Woolcock, Infect. Immun. 10:568 (1974)].

Group G streptococci have also been reported to cause a wide range of human infections. Although it is uncertain whether the virulence of these organisms is always due to the presence of an M-like cell surface protein, it may be that it is. Examination of three strains of group G streptococci isolated from human infections revealed the presence in the strains of a type 12M cell surface protein [Maxted and Potter, J. Genl. Microbiol. 49:119 (1967)].

Among the group A strains tested were three that are functionally M⁻ (i.e., they do not produce protective M protein and are thus phagocytized). The DNA from two of these M⁻ strains nevertheless hybridized with the emm6 gene probe, showing that they retain at least some of the emm gene intact. Presumably, these strains are mutants whose emm gene product is either nonfunctional or synthesized in reduced amount. The DNA from one M⁻ strain did not hybridize with the probe, suggesting that in that strain the emm gene was substantially deleted.

The results of the dot blot tests were confirmed by a study in which DNA from various M type group A streptococcal strains was extracted and digested with NciI and HindIII. Samples of the resulting fragments of DNA were then separated by agarose gel electrophoresis as described by Maniatis et al., supra, 150–161, and hybridized with the emm6 $^{32}$P-labeled probe, and the positions of the hybrid DNA fragments were revealed by autoradiography. The results are shown in FIG. 5.

In FIG. 5, lane 1 represents 10.9, 7.74, 5.15, 2.44, 1.80 and 0.60 kb DNA molecular size markers that had been labeled with $^{32}$p. Lanes 2 through 10 contained the probe-hybridized NciI/HindIII fragments of DNA from streptococci of M types 6, 47, 5, 19, 26, 11, 24, 12 and 23, respectively. In each case, there were two or more DNA fragments that hybridized with the probe. As expected from the dot blot studies, DNA from M⁻ strain T28/51/4 (lane 11) did not hybridize, while that from M⁺ strain T28/150A/5 (lane 12) did.

7. DEPOSITS OF MICROORGANISMS

The following listed *E. coli* strains carrying the listed plasmid have been deposited with the Agricultural Research Culture Collection (NRRL), Peoria, Ill., and have been assigned the following accession numbers:

| *E. coli* strain | Plasmid | Accession Number |
|---|---|---|
| K-12, C600NR Lambda cI857 | pJRS42.13 | NRRL B-15529 |
| K-12, C600NR Lambda cI857 | pJRS42 | NRRL B-15535 |

The present invention is not to be limited in scope by the microorganisms deposited, since the deposited microorganisms are intended to be illustrative of several aspects of the invention. Indeed, various modifications of the invention in addition to those shown and described herein will become apparent to those skilled in the art from the foregoing description and accompanying drawings. Such modifications are intended to fall within the scope of the appended claims.

In the present specification the base pair sizes given for nucleotides are approximate and are used for purposes of description.

We claimed:

1. An isolated polypeptide comprising a streptococcal M6 protein.

2. A polypeptide according to claim 1 wherein said polypeptide produces opsonic antibodies to type 6 streptococci when injected into rabbits.

3. A composition of matter comprising a polypeptide according to claim 1 and a carrier therefor.

4. A polypeptide comprising a streptococcal M6 protein, said polypeptide having been produced by a unicellular organism by a process comprising the steps of introducing a recombinant plasmid having a DNA sequence coding for said polypeptide into said organism, said plasmid being capable of being replicated, transcribed and translated by said organism, and culturing the organism in a nutrient broth.

5. A polypeptide according to claim 4, wherein the unicellular organism is gram positive.

6. A polypeptide according to claim 4, wherein the unicellular organism is gram negative.

7. A polypeptide according to claim 4, wherein the unicellular organism is *Escherichia coli*.

8. A polypeptide according to claim 4, wherein said polypeptide produces opsonic antibodies to type 6 streptococci when injected into rabbits.

* * * * *